United States Patent [19]

Kondo et al.

[11] 3,970,673
[45] July 20, 1976

[54] PROCESS FOR PREPARING BICYCLIC γ-LACTONE

[75] Inventors: Kiyosi Kondo, Yamato; Masakatsu Matsumoto, Sagamihara; Fumio Mori, Kurashiki, all of Japan

[73] Assignee: Sagami Chemical Research Center, Tokyo, Japan

[22] Filed: May 29, 1975

[21] Appl. No.: 582,002

[30] Foreign Application Priority Data

May 29, 1974 Japan.............................. 49-59637
Sept. 26, 1974 Japan............................ 49-109977

[52] U.S. Cl.................. 260/343.3 R; 252/522; 260/468 K; 260/615 A
[51] Int. Cl.²............... C07D 307/77; C07D 307/93
[58] Field of Search................... 260/343.3

[56] References Cited
UNITED STATES PATENTS 3,077,496  2/1963  Julia..................................... 260/514
3,299,100  1/1967  Phillips........................... 260/343.6

*Primary Examiner*—James A. Patten
*Attorney, Agent, or Firm*—Sughrue, Rothwell, Mion, Zinn & Macpeak

[57] ABSTRACT

A process for preparing a bicyclic γ-lactone represented by the formula (I)

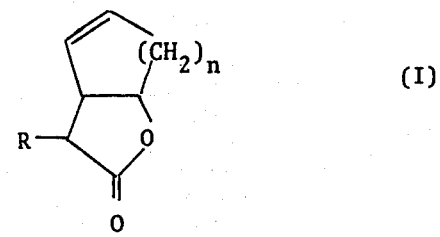

wherein R represents a hydrogen atom or a straight or branched chain alkyl group having 1 to 4 carbon atoms and $n$ is an integer of 1 to 6, which comprises condensing a cycloalkene diol compound represented by the formula (II)

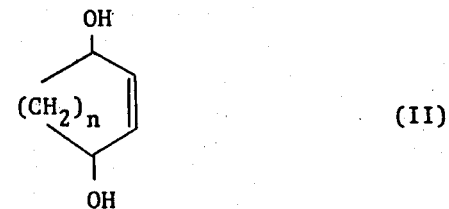

wherein $n$ is as defined above, with an orthocarboxylic acid ester represented by the formula (III)

$$R-CH_2-C(OR^1)_3 \qquad (III)$$

wherein R is as defined above and $R^1$ represents a straight or branched chain alkyl group having 1 to 4 carbon atoms, in the presence of an acidic catalyst.

7 Claims, No Drawings

PROCESS FOR PREPARING BICYCLIC γ-LACTONE

BACKGROUND OF THE INVENTION

1. Field of the Invention

This invention relates to a process for preparing a bicyclic γ-lactone and, more particularly, it relates to an improvement in the process for preparing a bicyclic γ-lactone represented by the formula (I)

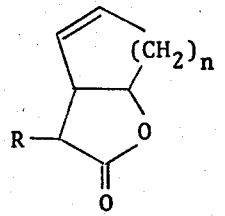

(I)

wherein R represents a hydrogen atom or a straight or branched chain alkyl group having 1 to 4 carbon atoms and n is an integer of 1 to 6.

2. Description of the Prior Art

The compounds of the formula (I) wherein n is 1 are well known to be useful as intermediates for the synthesis of prostaglandins as described in E. J. Corey and T. Ravindranathan, *Tetrahedron Letters*, 4753 (1971) and J. J. Partridge et al, *Journal of the American Chemical Society*, 95:21, 7171 (1973). Also, the compounds of the formula (I) wherein n is 2, 3 or 4 are useful since they constitute a partial structure of bicyclic γ-lactones having physiological activities such as anti-cancer and antimicrobial activities which have recently been considered to be useful. The compounds of the formula (I) wherein n is 3 to 6 generally possess fragrance and are expected to be useful as perfumes or as intermediates for the synthesis of perfumes.

A typical conventional method for the synthesis of bicyclic lactones comprises condensing a cycloalkadiene with dichloroacetic acid chloride in the presence of triethylamine followed by a zinc treatment in acetic acid, and reacting the resulting product with hydrogen peroxide, as described in E. J. Lorey et al, *Tetrahedron Letters*, 311 (1970). However, this conventional method requires a number of steps and in addition requires an expensive starting material, dichloroacetic acid chloride and an expensive reagent, triethylamine, and therefore is not said to be an economical method. Further, the above conventional method has a disadvantage in that it produces a large amount of undesirable substances as by-products thereby decreasing the yield of the desired bicyclic lactones. Such formation of the by-products not only renders the method uneconomical but also requires additional steps for purifying the product.

SUMMARY OF THE INVENTION

As a result of extensive studies on the process for preparing bicyclic γ-lactones which is advantageous in the production on an industrial scale, it was found that the bicyclic γ-lactones represented by the formula (I) can be prepared conveniently from the corresponding cycloalkene diol and an orthocarboxylic acid ester.

A primary object of this invention is therefore to provide a process for preparing a bicyclic γ-lactone represented by the formula (I)

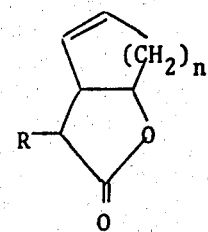

(I)

wherein R represents a hydrogen atom or a straight or branched chain alkyl group having 1 to 4 carbon atoms and n is an integer of 1 to 6, which comprises condensing a cycloalkene diol compound represented by the formula (II)

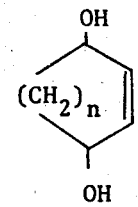

(II)

wherein n is as defined above, with an orthocarboxylic acid ester represented by the formula (III)

$R-CH_2-C(OR^1)_3$ (III)

wherein R is as defined above and $R^1$ represents a straight or branched chain alkyl group having 1 to 4 carbon atoms, in the presence of an acidic catalyst.

DETAILED DESCRIPTION OF THE INVENTION

The term "a straight or branched chain alkyl group having 1 to 4 carbon atoms" used herein for the substituents R and $R^1$ includes methyl, ethyl, n-propyl, isopropyl, n-butyl, sec-butyl and tert-butyl groups.

Examples of the cycloalkene diol compounds of the formula (II) which can be used in the present invention are preferably those having n of 1 to 4 such as cis-cyclopent-2-ene-1,4-diol (n=1), cis-cyclohex-2-ene-1,4-diol (n=2), cis-cyclohept-2-ene-1,4-diol (n=3), cis-cyclooct-2-ene-1,4-diol (n=4) and the like.

The cycloalkene diol compounds of the formula (II) can be easily prepared by the addition reaction of oxygen in a singlet state to a cycloalkadiene which is readily available as an industrial raw material, followed by reduction of the resulting addition product.

The orthocarboxylic acid esters which can be used in the present invention represented by the formula (III) can be obtained by a well-known procedure, for example, by alcoholysis of the corresponding nitriles. A typical example of the orthocarboxylic acid esters is an ethyl ester.

Representative examples of the acidic catalysts which can be used in the process of this invention are phenols such as phenol, o-, m- or p-nitrophenol, o-, m- or p-cresol, o-, m- or p-xylenol, 2,6-dimethylphenol, 2,6-di-t-butylphenol, 2,4,6-tri-sec-butylphenol, 2,4,6-tri-t-butylphenol, 4-methyl-2,6-di-t-butylphenol, 4-methyl-3,5-di-t-butylphenol, hydroquinone, 2,5-di-t-butylhydroquinone, α,β-naphthol and the like, aliphatic acids such as acetic acid, propionic acid, butyric acid, isobutyric acid, cyclohexane-carboxylic acid, valeric acid, succinic acid, adipic acid and the like, aromatic carboxylic acids such as benzoic acid, m-chlorobenzoic acid and the like, sulfonic acids such as benzenesulfonic acid, p-toluenesulfonic acid and the like, inorganic acids such as hydrochloric acid, sulfuric acid, phosphoric acid, boric acid and the like, and Lewis acids such as aluminum chloride, zinc chloride, ferric chloride, boron trifluoride, mercuric acetate and the like. Of these acidic catalysts, preferred examples are hydroquinones, phenols, aliphatic acids having 2 to 6 carbon atoms, aromatic carboxylic acids and inorganic acids, e.g., phosphoric acid and boric acid, etc. since, with these preferred acidic catalysts, the reaction generally proceeds smoothly. These acidic catalysts are generally used in a proportion of about 0.001 to about 20% by weight, preferably 1 to 15% by weight, with respect to the amount of the cycloalkene diol compound of the formula (II).

The condensation reaction between the cycloalkene diol compound of the formula (II) and the orthocarboxylic acid ester of the formula (III) can be carried out in the presence or absence of solvents, in a molar ratio of about 1 to about 5 moles, preferably 1 to 2 moles, of the orthocarboxylic acid ester of the formula (III) per mole of the cycloalkene diol compound of the formula (II).

Examples of the solvents which can be used in the present invention are those which do not adversely affect the reaction as well as the starting materials and the desired product and those having a boiling point ranging from about 120°C to about 170°C, for example, paraffins, n-octane, o-, m- or p-xylene, di-n-butyl ether, N,N-dimethylformamide and the like.

As described above, the condensation reaction of this invention can be effected without using solvents. In such a case, use of an excess of the orthocarboxylic acid ester of the formula (III), e.g., about 2 to about 5 moles of the ester (III), per mole of the cycloalkene diol compound of the formula (II) is preferred in order to serve as both the reactant and the solvent.

The condensation reaction in accordance with the process of this invention can be carried out while heating the reaction mixture at a temperature of about 120° to about 170°C, preferably from 130° to 160°C. At a temperature below about 120°C, the reaction rate is generally low and at a temperature above about 170°C, the yield of the desired product tends to decrease due to the formation of by-products.

As will be apparent to one skilled in the art, the time required for completing the reaction generally varies depending upon the molar ratio of the reactants, the reaction temperature and other reaction conditions used, for example, the type and the amount of solvents, etc. However, generally, a reaction time from about 2 to about 15 hours provides a satisfactory result.

The reaction scheme according to the present invention can be illustrated below with reference to a specific embodiment using an orthoacetic acid ester as an example of the orthocarboxylic acid ester of the formula (III), but the present invention is not limited to such a specific example.

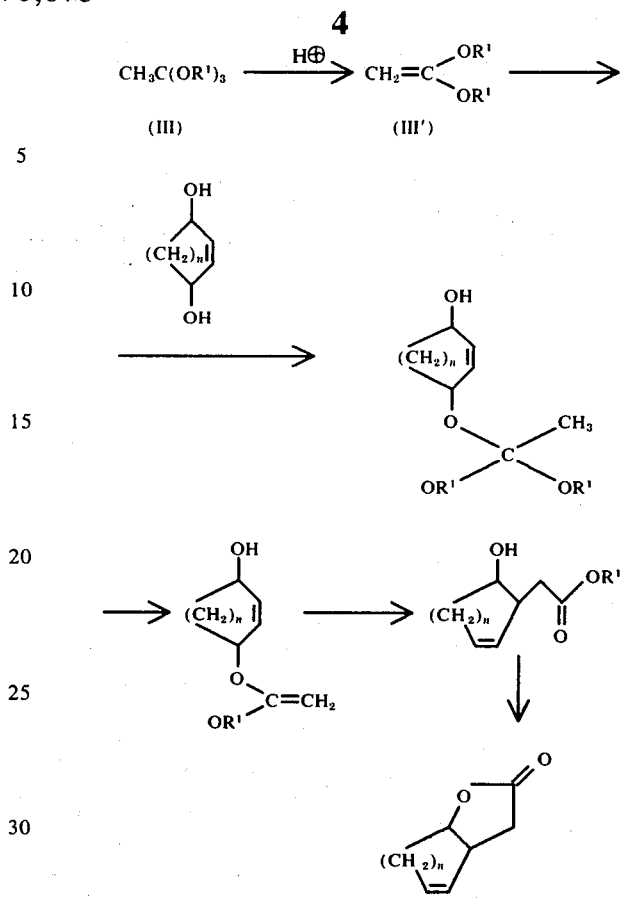

wherein $R^1$ and n are as defined previously.

As will be apparent from the above reaction scheme, a ketene acetal of the formula (III') functions in the same manner as the orthocarboxylic acid ester (III) and, therefore, can be used in place of the orthocarboxylic acid ester. It is to be understood that the present invention is contemplated to include the use of a ketene acetal corresponding to the orthocarboxylic acid ester of the formula (III).

The present invention is further illustrated by the following examples, but they are given for illustrative purposes only and are not to be construed as limiting the present invention. Unless otherwise indicated, all parts, percents, ratios and the like are by weight.

EXAMPLE 1

0.5 Part of hydroquinone was added to a mixture of 5 parts of cis-3,5-dihydroxy-1-cyclopentene and 16.2 parts of ethyl orthoacetate, and the resulting mixture was allowed to react at a temperature of 145° to 155°C for 12 hours with stirring. The reaction mixture was then distilled under reduced pressure to recover 6 parts of unreacted ethyl orthoacetate, and then a fraction boiling at 73° to 75°C/0.3 mmHg was distilled out to obtain 4.3 parts of the desired product, a lactone of cis-2-hydroxy-cyclopent-4-ene-1-acetic acid. The IR spectral data of the product thus obtained was found to be quite consistent with those reported in P. A. Brieco, *J. Org. Chem.*, 37, 2363 (1972). The yield of the isolated product with respect to the diol starting material was 69%.

EXAMPLE 2

In the same manner as described in Example 1 but using 0.5 part of phenol in place of the hydroquinone, 7 parts of unreacted ethyl orthoacetate was recovered and then 4.2 parts of the desired product, a lactone of cis-2-hydroxy-cyclopent-4-ene-1-acetic acid was obtained.

EXAMPLE 3

In the same manner as described in Example 1 but using 0.3 part of isobutyric acid in place of the hydroquinone, 10 parts of unreacted ethyl orthoacetate was recovered and then 3.4 parts of the desired product, a lactone of cis-2-hydroxy-cyclopent-4-ene-1-acetic acid was obtained.

EXAMPLE 4

0.3 Part of hydroquinone was added to a mixture of 3 parts of cis-3,5-dihydroxy-3-cyclopentene and 11.3 parts of ethyl orthoacetate, and the resulting mixture was allowed to react at a temperature of 140° to 150°C for 6 hours while stirring. The reaction mixture was then distilled under reduced pressure to recover any unreacted ethyl orthoacetate, and then a fraction boiling at 74°C/0.3 mmHg was distilled out to obtain 3.1 parts of the desired product, a lactone of cis-2-hydroxy-cyclopent-4-ene-1-acetic acid. The IR spectral data of the product thus obtained was found to be quite consistent with those reported by P. A. Grieco, *J. Org. Chem.*, 37, 2363 (1972). The yield of the isolated product with respect to the diol starting material was 85%.

EXAMPLE 5

20 Parts of cis-cyclohex-2-ene-1,4-diol and 1 part of hydroquinone were dissolved in 100 parts of ethyl orthoacetate, and the resulting solution was heated at a temperature of 150°C for 6 hours while removing continuously the ethanol produced as a by-product from the reaction mixture by distillation. After completion of the reaction, any unreacted ethyl orthoacetate was removed from the reaction mixture by distillation and then the resulting residue was distilled under reduced pressure to obtain 20 parts (85% yield) of a lactone of 2-hydroxy-cyclohex-5-ene-1-acetic acid as an oily substance having a boiling point of 78°C at 0.16 torr. On the IR spectral analysis, the product thus obtained showed a strong absorption at 1775 cm$^{-1}$.

EXAMPLE 6

A mixture of 26 parts of cis-cyclohept-2-ene-1,4-diol, about 3 parts of hydroquinone and 100 parts of ethyl orthoacetate was heated at a temperature of 150° to 155°C for 8 hours while continuously removing the ethanol produced as a by-product from the reaction mixture by distillation. The resulting reaction mixture was then worked up in the same manner as described in Example 5 to obtain 25 parts (83% yield) of a lactone of 2-hydroxy-cyclohept-6-ene-1-acetic acid as an oily substance having a strong fragrance. The product thus obtained had a boiling point of 95°C at 0.28 torr and showed, on the IR spectral analysis, a strong absorption at 1775 cm$^{-1}$.

EXAMPLE 7

23 Parts of cis-cyclooct-2-ene-1,4-diol and 2 parts of hydroquinone were dissolved in 100 parts of ethyl orthoacetate, and the resulting mixture was heated at a temperature of 140° to 150°C for 12 hours followed by heating at a temperature of 150° to 160°C for 4 hours while removing continuously the ethanol produced as a by-product from the reaction mixture by distillation. The resulting reaction mixture was then worked up in the same manner as described in Example 5 to obtain 11.6 parts (43% yield) of a lactone of 2-hydroxy-cyclooct-7-ene-1-acetic acid as an oily substance having a strong fragrance. The product thus obtained had a boiling point of 103°C at 0.22 torr and showed, on the IR spectral analysis, a strong absorption at 1780 cm$^{-1}$.

While the invention has been described in detail and with reference to the specific embodiments thereof, it will be apparent to one skilled in the art that various changes and modifications can be made therein without departing from the spirit and the scope thereof.

What is claimed is:

1. A process for preparing a bicyclic γ-lactone represented by the formula (I)

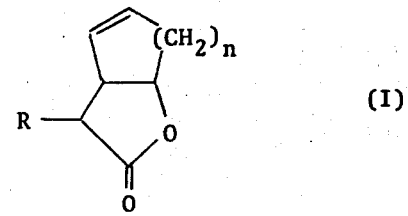

wherein R represents a hydrogen atom or a straight or branched chain alkyl group having 1 to 4 carbon atoms and n is an integer of 1 to 6, which comprises condensing a cycloalkene diol compound represented by the formula (II)

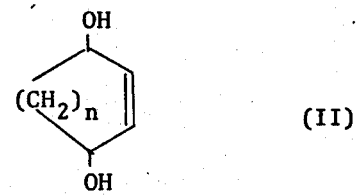

wherein n is as defined above, with an orthocarboxylic acid ester represented by the formula (III)

wherein R is as defined above and R$^1$ represents a straight or branched chain alkyl group having 1 to 4 carbon atoms, in the presence of an acidic catalyst at a temperature of about 120°C to about 170°C in a molar ratio of about 1 to about 5 moles of said orthocarboxylic acid ester per mole of said cycloalkene diol compound.

2. The process according to claim 1, wherein n represents an integer of 1 to 4.

3. The process according to claim 1, wherein said condensation is conducted in the presence of a solvent having a boiling point ranging from about 120°C to about 170°C.

4. The process according to claim 3, wherein said solvent is a paraffin, n-octane, o-, m- or p-xylene, di-n-butyl ether or N,N-dimethylformamide.

5. The process according to claim 1, wherein said acidic catalyst is used in a proportion of about 0.001 to about 20% by weight with respect to the amount of said cycloalkene diol compound.

6. The process according to claim 1, wherein sid acidic catalyst is a phenol, an aliphatic acid, an aromatic carboxylic acid, a sulfonic acid, an inorganic acid or a Lewis acid.

7. The process according to claim 1, wherein said cycloalkene diol compound is cis-cyclopent-2-ene-1,4-diol, cis-cyclohex-2-ene-1,4-diol, cis-cyclohept-2-ene-1,4-diol or cis-cyclooct-2-ene-1,4-diol.

* * * * *